United States Patent [19]

Whitten et al.

[11] Patent Number: 5,567,710
[45] Date of Patent: Oct. 22, 1996

[54] POLYCYCLIC FUSED RING MODULATORS OF ACETYLCHOLINE RECEPTORS

[75] Inventors: Jeffrey P. Whitten; Ian A. McDonald; Jean-Michel Vernier, all of San Diego, Calif.

[73] Assignee: SIBIA Neurosciences, Inc., La Jolla, Calif.

[21] Appl. No.: 322,757

[22] Filed: Oct. 13, 1994

[51] Int. Cl.$^6$ ............... A61K 31/44; C07D 471/04; C07D 491/147
[52] U.S. Cl. ............... 514/292; 514/293; 546/81; 546/83; 546/84; 546/88
[58] Field of Search ............... 546/81, 83, 84, 546/88; 514/292, 293

[56] References Cited

U.S. PATENT DOCUMENTS 5,399,575  3/1995  Friebe et al. ............... 574/340
5,418,229  5/1995  Alker et al. ............... 514/220

OTHER PUBLICATIONS

Glassco W, Suchocki J, George C, Martin B R & May E L. (1993) J. Med. Chem. 36, 3381–3385.

Albanese et al., "Chronic Administration of 1–Methyl–4–Phenyl–1,2,3,6–Tetrahydropyridine to Monkeys: Behavioural, Morphological and Biochemical Correlates" *Neuroscience* 55:823–832 (1993).

Brandsma et al., "3–Deuterio– and (3–Methylthio)Pyridine" *Preparative Polar Organometallic Chemistry* 1:172–173 (1987).

Brioni et al., "Nicotinic receptor agonists exhibit anxiolytic–like effects on the elevated plus–maze test" *Eur. J. Pharmacol.* 238:1–8 (1993).

Chorvat et al., "Total Synthesis of 2–Azaestratrienes" *J. Org. Chem.* 43(5):966–972 (1978).

Christensen et al., "On the Supersensitivity of Dopamine Receptors, Induced by Neuroleptics" *Psychoparmacol.* 48:1–6 (1976).

Clow et al., "Changes in Dopamine–Mediated Behaviour During One Year's Neuroleptic Administration" *Euro. J. Pharmacol.* 57:365–375 (1979).

Colpaert, F. C., "Pharmacological Characteristics of Tremor, Rigidity and Hypokinesia Induced by Reserpine in Rat" *Neuropharmacol.* 26(9):1431–1440 (1987).

Cordonnier and Sliwa, "Synthesis of New Funcatmental Heterocycles, Part VIII. A New Syntheiss of 2H–Pyrano[3,2–c] pyridine" *J. Chem. Research* vol. 124 (1979).

Coyle et al., "Kainic Acid: Insights from a Neurotoxin into the Pathophysiology of Huntington's Disease" *Neurobehav. Toxicol. Tetatol.* 5:617–624 (1983).

D'Amour and Smith, "A Method for Determining Loss of Pain Sensation" *J. Pharmacol. Exp. Ther.* 72:74–79 (1941).

Emerich et al., "Nicotine Potentiates Haloperidol–Induced Catalepsy and Locomotor Hypoactivity" *Pharmacol. Biochem. Behav.* 38:875–880 (1991).

Estrella et al., "A further study of the neuromuscular effects of vesamicol (AH5183) and of its enantiomer specificity" *Br. J. Pharmacol.* 93:759–768 (1988).

Flynn and Mash, "Characterization of L–[$^3$H]Nicotine Binding in Human Cerebral Cortex: Comparison Between Alzheimer's Disease and the Normal" *J. Neurochemistry* 47(6):1948–1954 (1986).

Garcia and Greco, "Facile Bromination of Pyridine–Type Heterocycles at the β–Position" *J. Am. Chem. Soc.* 82:4430–4431 (1960).

Iwamoto, Edgar T., "Antinociception after Nicotine Administration into the Mesopontine Tegmentum of Rats: Evidence for Muscarinic Actions" *J. Pharmacol. Exp. Ther.* 251(21):412–421 (1989).

Janson et al., "Differential effects of acute and chronic nicotine treatment on MPTP–(1–methyl–4–phenyl–1,2,3,6–tetrahydropyridine) induced degeneration of nigrostriatal dopamine neurons in the black mouse" *Clin. Investig.* 70:232–238 (1992).

Klockgether and Turski, "NMDA Antagonists Potentiate Antiparkinsonian Actions of $_L$–Dopa in Monoamine–depleted Rats" *Ann. Neurol.* 28:539–546 (1990).

Miyata et al., "Role of the Serotonin$_3$ Receptor in Stress––Induced Defecation" *J. Pharmacol. Exp. Ther.* 261(1):297–303 (1992).

Pellow et al., "Validation of open: closed arm entries in an elevated plus–maze as a measure of anxiety in the rat" *Neurosci. Meth.* 14:149–167 (1985).

Ranganathan et al., "Nitroethylene: A Stable, Clean, and Reactive Agent for Organic Synthesis" *J. Org. Chem.* 45:1185–1189 (1980).

Rupniak et al., "Cholinergic Manipulation of Perioral Behaviour Induced by Chronic Neuroleptic Administration to Rats" *Psychopharmacol.* 79:226–230 (1983).

Sacaan et al., "Metabotropic Glutamate Receptor Activation Produces Extrapyramidal Motor System Activation That is Mediated by Striatal Dopamine" *J. Neurochem.* 59(1):245 (1992).

Scharcz et al., "Quinolinic Acid: An Endogenous Metabolite That Produces Axon–Sparing Lesions in Rat Brain" *Science* 219:316–318 (1983).

Sershen et al., "Behavioral and Biochemical Effects of Nicotine in an MPTP–Induced Mouse Model of Parkinson's Disease" *Pharmacol. Biochem. Behav.* 28:299–303 (1987).

Sundstrom et al., "Chronic neurochemical and behavioral changes in MPTP–lesioned C57BL/6 mice: a model for Parkinson's disease" *Brain Res.* 528:181–188 (1990).

(List continued on next page.)

*Primary Examiner*—C. Warren Ivy
*Assistant Examiner*—Evelyn Huang
*Attorney, Agent, or Firm*—Pretty Schroeder Brueggemann & Clark; Stephen E. Reiter

[57] ABSTRACT

In accordance with the present invention, there is provided a class of polycyclic fused ring compounds which are modulators of acetylcholine receptors. The compounds of the invention displace acetylcholine receptor ligands from their binding sites. Invention compounds may act as agonists, partial agonists, antagonists or allosteric modulators of acetylcholine receptors.

17 Claims, No Drawings

OTHER PUBLICATIONS

Ungerstedt et al., "Animal Models of Parkinsonism" *Adv. Neurol.* 3:257–271 (1973).

Ungerstedt and Arbuthnott, "Quantitative Recording of Rotational Behavior in Rats After 6–Hydroxy–Dopamine Lesions of the Nigrostriatal Dopamine System" *Brain Research* 24:485–493 (1970).

Von Voightlander and Moore, "Turning Behavior of Mice with Unilateral 6–Hydroxydopamine Lesions in the Striatum: Effects of Apomorphine, $_L$–Dopa, Amantadine, Amphetamine and Other Psychomotor Stimulants" *Neuropharmacology* 12:451–462 (1973).

Waddington et al., "Spontaneous Orofacial Dyskinesia and Dopaminergic Function in Rats After 6 Months of Neuropeptic Treatment" *Science* 220:530–532 (1983).

Williams et al., "Stress–Induced Changes in Intestinal Transit in the Rat: A Model for Irritable Bowel Syndrome" *Gastroenterology* 94:611–621 (1988).

Williams et al., "Neuronal Nicotinic Acetylcholine Receptors" *Drug News & Perspectives* 7(4):205–223 (1994).

Yamada et al., "Effects of a thienylalkylamine derivative, T–1815, on colonic propulsion in mice and rats" *Jpn. J. Pharmacol.* 58 (Suppl.):131 (1992).

Alkondon and Albuquerque, "Diversity of Nicotinic Acetylcholine Receptors in Rat Hippocampal Neurons. III. Agonist Actions of the Novel Alkaloid Epibatidine and Analysis of Type II Current" *J. Pharmacol. Exper. Therap.* 274:771–782 (1995).

Anderson et al., "Characterization of [$^3$H]ABT–418: A Novel Cholinergic Channel Ligand" *J. Pharmacol. Exper. Therap.* 273:1434–1441 (1995).

Chaki et al., "Design and Syntheses of 4–Acylaminopyridine Derivatives: Novel High Affinity Choline Uptake Enhancers I$^1$" *Bioorgan. & Med. Chem. Let.* 5:1489–1494 (1995).

De Fiebre et al., "Characterization of a Series of Anabaseine–Derived Compounds Reveals That the 3–(4)–Dimethylaminocinnamylidine Derivative Is a Selective Agonist at Neuronal Nicotinic $\alpha 7/^{125}$I–$\alpha$–Bungarotoxin Receptor Subtypes" *Mol. Pharmacol.* 47:164–171 (1995).

Hansson et al., "On the Quantitative Structure—Activity Relationships of Meta–Substituted (S)–Phenylpiperidines, a Class of Preferential Dopamine $D_2$ Autoreceptor Ligands: Modeling of Dopamine Synthesis and Release in Vivo by Means of Partial Least Squares Regression" *J. Med. Chem.* 38:3121–3131 (1995).

Kashiwabara et al., "Comparative Vasodepressor Effects of 3–Pyridine Derivatives Possessing the Cyanoamidine or Amide Structure in Pithed Rats" *Arch. int. Pharmacodyn* 328:297–306 (1994).

Natsugari et al., "Novel, Potent, and Orally Active Substance P Antagonists: Synthesis and Antagonist Activity of N–Benzylcarboxamide Derivatives of Pyrido[3,4–b]pyridine" 38:3106–3120 (1995).

Glassco et al., "Synthesis, Optical Resolution, Absolute Configuration, and Preliminary Pharmacology of (+)–and (−)–cis–2,3,3a,4,5,9b–Hexahydro–1–methyl–1H–pyrrolo–[3,2–h]isoquinoline, a Structural Analog of Nicotine" *J. Med. Chem.* 36:3381–3385 (1993).

POLYCYCLIC FUSED RING MODULATORS OF ACETYLCHOLINE RECEPTORS

The present invention relates to novel polycyclic fused ring compounds which are capable of modulating acetylcholine receptors. Invention compounds are useful, for example, for treatment of dysfunction of the central or autonomic nervous systems including dementia, cognitive disorders, neurodegenerative disorders, extrapyramidal disorders, convulsive disorders, cardiovascular disorders, neurocrine disorders, pain, gastrointestinal disorders, and drug abuse. In addition, the present invention relates to pharmaceutical compositions containing these compounds, as well as various uses therefor.

BACKGROUND OF THE INVENTION

By modulation of neurotransmitter release (including dopamine, norepinephrine, acetylcholine) from different brain regions, acetylcholine receptors are involved in the modulation of neuroendocrine function, respiration, mood, motor control and function, memory and cognition, and the mechanisms of substance abuse. Ligands for acetylcholine receptors have been demonstrated to have effects on cognition, appetite, substance abuse, memory, cardiovascular function, pain and gastrointestinal motility and function. The distribution of acetylcholine receptors that bind nicotine, i.e., nicotinic acetylcholine receptors, is widespread in the brain, including the basal ganglia, limbic system, cerebral cortex and mid- and hind-brain nuclei. In the periphery, the distribution includes muscle, autonomic ganglia, gastrointestinal tract and cardiovascular system.

Acetylcholine receptors have been shown to be decreased in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds which can selectively modulate the activity of acetylcholine receptors. In response to such need, the present invention provides a new family of polycyclic fused ring compounds which modulate acetylcholine receptors.

BRIEF DESCRIPTION OF THE INVENTION

In accordance with the present invention, we have discovered that the class of polycyclic fused ring compounds defined herein are modulators of acetylcholine receptors.

The compounds of the present invention are capable of displacing one or more acetylcholine receptor ligands, e.g., $^3$H-nicotine, from mammalian cerebral membrane binding sites. Invention compounds may act as agonists, partial agonists, antagonists or allosteric modulators of acetylcholine receptors. Therapeutic indications for compounds with activity at acetylcholine receptors include diseases of the central nervous system such as Alzheimer's disease and other disorders involving memory loss and/or dementia (including AIDS dementia); disorders of extrapyramidal motor function such as Parkinson's disease, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulimia and anorexia; disorders of nociception and control of pain; autonomic disorders including dysfunction of gastrointestinal motility and function such as irritable bowel syndrome, diarrhea, constipation, gastric acid secretion and ulcers; pheochromocytoma; cardiovascular dysfunction including hypertension and cardia arrhythmias, as well as co-medication uses in surgical applications.

DETAILED DESCRIPTION OF THE INVENTION

In accordance with the present invention, there are provided compounds having the structure (Formula I):

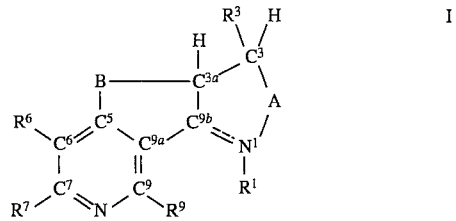

wherein:

A is a 1, 2 or 3 atom bridging species which forms part of a 5-, 6- or 7-membered ring including $N^1$, $C^{9b}$, $C^{3a}$ and $C^3$; and B is a 1, 2 or 3 atom bridging species which forms part of a 5-, 6- or 7-membered ring including $C^5$, $C^{9a}$, $C^{9b}$, and $C^{3a}$; and $R^1$ is selected from hydrogen, lower alkyl, aryl, substituted aryl, alkylaryl, or substituted alkylaryl, or $R^1$ is absent when there is a double bond between $N^1$ and $C^{9b}$; and $R^3$ is selected from hydrogen or a lower alkyl moiety; and $R^6$ and $R^7$ are independently selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heteroaryl, substituted heteroaryl, acyl, halogen, trifluoromethyl, trialkylsilyl, triarylsilyl, cyano, nitro, —S(O)—R', —S(O)$_2$—R', —S(O)$_2$—NHR', —C(O)—NHR' or —NH—C(O)—R', wherein each R' is lower alkyl or aryl; —OR", —NR"$_2$ or —SR", wherein each R" is independently selected from hydrogen, lower alkyl, aryl, substituted aryl, alkylaryl or substituted alkylaryl; and $R^9$ is selected from hydrogen or lower alkyl;

with the proviso that, when A is —CH$_2$—, B is —CH$_2$CH$_2$—, and each of $R^3$, $R^6$, $R^7$ and $R^9$ are —H then $R^1$ is not —H or —CH$_3$.

As employed herein, "lower alkyl" refers to straight or branched chain alkyl radicals having in the range of about 1 up to 4 carbon atoms; "alkyl" refers to straight or branched chain alkyl radicals having in the range of about 1 up to 12 carbon atoms; "substituted alkyl" refers to alkyl radicals further bearing one or more substituents such as hydroxy, alkoxy (of a lower alkyl group), mercapto (of a lower alkyl group), halogen, trifluoromethyl, cyano, nitro, amino, carboxyl, carbamato, sulfonyl, sulfonamido, and the like;

"alkenyl" refers to straight or branched chain hydrocarbyl radicals having at least one carbon-carbon double bond, and having in the range of about 2 up to 12 carbon atoms and "substituted alkenyl" refers to alkenyl radicals further bearing one or more substituents as set forth above;

"alkynyl" refers to straight or branched chain hydrocarbyl radicals having at least one carbon-carbon triple bond, and having in the range of about 2 up to 12 carbon atoms, and "substituted alkynyl" refers to alkynyl radicals further bearing one or more substituents as set forth above;

"aryl" refers to aromatic radicals having in the range of 6 up to 14 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"aroyl" refers to aryl-carbonyl species such as benzoyl and "substituted aroyl" refers to aroyl radicals further bearing one or more substituents as set forth above;

"heteroaryl" refers to aromatic radicals containing one or more heteroatoms (e.g., N, O, S, or the like) as part of the aromatic ring, and having in the range of 3 up to 14 carbon atoms and "substituted heteroaryl" refers to heteroaryl radicals further bearing one or more substituents as set forth above;

"acyl" refers to alkyl-carbonyl species;

"halogen" refers to fluoride, chloride, bromide or iodide radicals;

"trialkylsilyl" refers to silyl radicals having three alkyl radicals (wherein the alkyl radicals can be the same or different and are as defined above); and "triarylsilyl" refers to silyl radicals having three aryl radicals (wherein the aryl radicals can be the same or different and are as defined above).

In one aspect of the present invention, bridging group A is a 1, 2 or 3 atom bridging species selected from alkylene, —C(O)— or —C(O)—substituted alkylene. Thus, A can be selected, for example, from —$CH_2$—, —$CH_2CH_2$—, —$CH_2CH_2CH_2$—, —C(O)—, —C(O)—$CH_2$—, —C(O)—$CH_2CH_2$—, and the like. Presently preferred compounds of the invention are those wherein A is selected from —$CH_2$—, —$CH_2CH_2$— or —$CH_2CH_2CH_2$—, with compounds having A as —$CH_2$— being the presently most preferred.

In accordance with another aspect of the present invention, bridging group B comprises a 1, 2 or 3 carbon alkylene, or a 1, 2 or 3 atom bridging species selected from —O—, —N($R^{10}$)—, —S—, —S(O)—, —S(O)$_2$—, or an —O—, —N($R^{10}$)—, —S—, —S(O)—, or —S(O)$_2$— containing alkylene moiety, wherein $R^{10}$ is a lower alkyl moiety. Thus, B can be selected, for example, from —$CH_2$—, —$CH_2CH_2$—, —$CH_2CH_2CH_2$—, —O—, —O—$CH_2$—, —O—$CH_2CH_2$—, —$CH_2$—O—$CH_2$—, —N($R^{10}$)—, —N($R^{10}$)—$CH_2$—, —N($R^{10}$)—$CH_2CH_2$—, —$CH_2$—N($R^{10}$)—$CH_2$—, —S—, —S—$CH_2$—, —S—$CH_2CH_2$—, —$CH_2$—S—$CH_2$—, —S(O)—, —S(O)—$CH_2$—, —S(O)—$CH_2CH_2$—, —$CH_2$—S(O)—$CH_2$—, —S(O)$_2$—, —S(O)$_2$—$CH_2$—, —S(O)$_2$—$CH_2CH_2$—, —$CH_2$—S(O)$_2$—$CH_2$—, and the like. Presently preferred compounds of the invention are those wherein B is —$CH_2CH_2$— or —O—$CH_2$—.

Additional preferred compounds of the invention are those wherein $R^1$ is selected from hydrogen or methyl; wherein $R^3$ is hydrogen; wherein $R^6$ is selected from hydrogen, halogen, alkyl, aryl, or substituted aryl (with hydrogen, bromine, chlorine, phenyl, paramethoxy phenyl, parahydroxy phenyl, paramercaptomethyl phenyl and paratrifluoromethyl phenyl being especially preferred); wherein $R^7$ is selected from hydrogen, alkyl or alkoxy (with hydrogen, methyl or methoxy being especially preferred); and wherein $R^9$ is hydrogen.

Particularly preferred compounds of the invention include the compound wherein A=—$CH_2$—, B=—$CH_2CH_2$—, $R^1$, $R^3$, $R^6$ and $R^9$=—H, and $R^7$=OCH$_3$; or wherein A=—$CH_2$—, B=—O—$CH_2$—, $R^1$, $R^3$, $R^6$, $R^7$ and $R^9$=—H, or wherein A=—$CH_2$—, B=—$CH_2CH_2$—, $R^1$=—$CH_3$, $R^3$, $R^6$ and $R^9$=—H, and $R^7$=—O—$CH_3$; or A=—$CH_2CH_2$—, B=—$CH_2CH_2$—, $R^1$, $R^3$, $R^6$ and $R^9$=—H, and $R^7$=—OCH$_3$.

Invention compounds have affinity for acetylcholine receptors. As employed herein, the term "acetylcholine receptor" refers to both nicotinic and muscarinic acetylcholine receptors. Affinity of invention compounds for such receptors can be demonstrated in a variety of ways, e.g., via competitive radioligand binding experiments in which the test compounds displace isotopically labelled ligands (such as nicotine, cystine, methylcarbamylcholine, quinuclidinyl benzilate, and the like) from binding sites in mammalian cerebral membranes. Furthermore, the binding of compounds to acetylcholine receptors can be evaluated as a functional response. For example, the activity of invention compounds can be evaluated employing functional assays based on recombinant neuronal acetylcholine receptor expression systems (see, for example, Williams et al., *Drug News & Perspectives* 7:205–223 (1994)). Test compounds can also be evaluated for their ability to modulate the release of neurotransmitters (e.g., dopamine, norepinephrine, and the like) from rat brain slices (e.g., striatum, hippocampus, and the like). See Examples 8 and 9 for further detail on such techniques. Moreover, test compounds can also be evaluated by way of behavioral studies employing animal models of various CNS, autonomic and cardiovascular disorders (see, for example, D'Amour and Smith, *J. Pharmacol. Exp. Ther.* 74–79 (1941), Iwamoto, *J. Pharmacol. Exp. Ther.* 251:412–421 (1989), Klockgether and Turski, *Ann. Neurol.* 28:539–546 (1990), Colpaert, F., *Neuropharmacology* 26:1431–1440 (1987), Ungerstedt and Arbutknott, *Brain Res.* 24:485–493 (1970), Von Voigtlander and Moore, *Neuropharmacology* 12:451–462 (1973), Ungerstedt et al., *Adv. Neurol.* 3:257–279 (1973), Albanese et al., *Neuroscience* 55:823–832 (1993), Janson et al., *Clin. Investig.* 70:232–238 (1992), Sundstrom et al., *Brain Res.* 528:181–188 (1990), Sershen et al., *Pharmacol. Biochem. Behav.* 28:299–303 (1987) for animal models of Parkinson's disease; Williams et al., *Gastroenterology* 94:611–621 (1988), Miyata et al., *J. Pharmacol. Exp. Ther.* 261:297–303 (1992), Yamada et al., *Jpn. J. Pharmacol.* 58 (Suppl.):131 (1992) for animal models of irritable bowel syndrome; Coyle et al., *Neurobehav. Toxicol. Tetatol.* 5:617–624 (1983), Schartz et al., *Science* 219:316–318 (1983) for animal models of Huntington's disease; Clow et al., *Euro. J. Pharmacol.* 57:365–375 (1979), Christensen et al., *Psychoparmacol.* 48:1–6 (1976), Rupniak et al., *Psychopharmacol.* 79:226–230 (1983), Waddington et al., *Science* 220:530–532 (1983) for animal models of tardive dyskinesia; Emerich et al., *Pharmacol. Biochem. Behav.* 38:875–880 (1991) for animal models of Gilles de la Tourette's syndrome; Brioni et al., *Eur. J. Pharmacol.* 238:1–8 (1993), Pellow et al., *J. Neurosci. Meth.* 14:149 (1985) for animal models of anxiety; and Estrella et al., *Br. J. Pharmacol* 93:759–768 (1988) for the rat phrenic nerve model which indicates whether a compound has ganglionic effects that may be useful in treating cardiovascular disorders).

Those of skill in the art recognize that invention compounds typically contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

In accordance with still another embodiment of the present invention, there are provided methods for the preparation of polycyclic fused ring compounds as described above. For example, many of the hexahydro-1H-pyrroloisoquinoline compounds described above can be prepared using synthetic chemistry techniques well known in the art from the cyclic ketone precursor of Formula III as outlined in Scheme I.

Scheme I

Step A

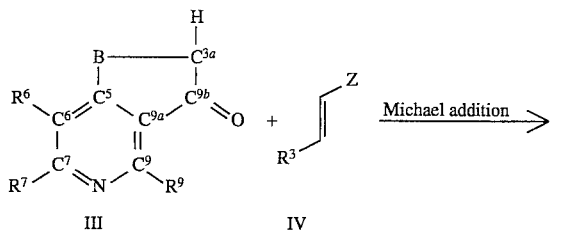

Step B

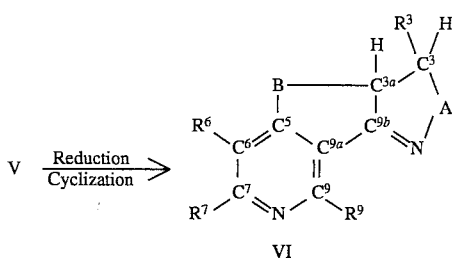

Step C

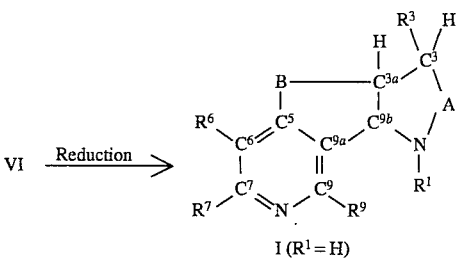

Step D

-continued
Scheme I

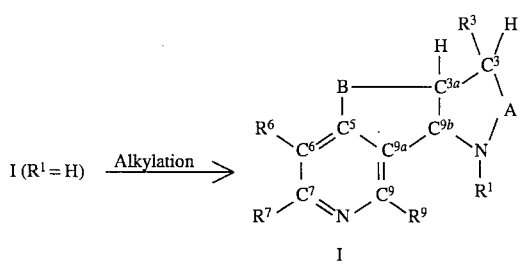

In step A of Scheme I, the cyclic ketone of Formula III is coupled to an alkene of Formula IV, where Z is represented by either a nitro group or a cyano group, to produce a pyridine of Formula V by a Michael addition reaction. The choice of a nitro or nitrile group in Formula IV will depend on the nature of the desired product. When A is a methylene radical, Z will be a nitro group; when A is an ethylene radical, Z will be a nitrile group.

The proper starting material in Step A of Reaction Scheme I is a cyclic ketone in which B is represented by the same methylene or ethylene function as that of the desired final product.

In step A, the cyclic ketone of Formula III is typically treated with about 1.0 up to 1.5 equivalents of a suitable base (such as lithium diisopropylamide (LDA)), followed by contact with 1 to 5 equivalents of alkene of Formula IV, in which Z is either a nitro group or a cyano group. The reactants are typically contacted at a temperature range of $-78°$ C. to room temperature ($\sim 25°$ C.) for a period of time ranging from 2 to 18 hours in a suitable solvent such as tetrahydrofuran. The alkenes of Formula IV are known in the art as are the methods for their preparation. The resulting pyridines of Formula V can then be purified by chromatographic techniques known in the art (such as, for example, flash chromatography).

In Step B of Scheme I, pyridine of Formula V is reduced employing techniques known in the art. Thus, the pyridine of Formula V is typically contacted in the presence of a transition metal catalyst (such as, for example, Raney Nickel), under an atmosphere of hydrogen at a pressure in the range of 10 to 55 pounds per square inch to produce a cyclic imine of Formula VI. The reduction is typically carried out at room temperature in a solvent such as methanol with 0.05 to 1 equivalent of the transition metal catalyst for a period of 8 to 48 hours. The imine of Formula VI can then be purified by chromatographic techniques known in the art such as flash chromatography.

In Step C, the imine is further reduced with a suitable hydride reducing agent (such as, for example, sodium cyanoborohydride) to give an amine of Formula I ($R^1$=H). Typically the imine of Formula VI is contacted with 1 to 3 equivalents of a suitable reducing agent, in a suitable solvent (such as methanol), with concurrent addition of an acid solution (e.g., HCl in dioxane), so as to maintain the reaction at a pH of 4 to 7. The reaction temperature is typically from 0° C. to room temperature for a period of 1 to 8 hours. The amine of Formula I is recovered from the reaction milieu by chromatographic techniques such as flash chromatography or recrystallization. If desired, the amine can be converted to an acid addition salt, such as a hydrobromide or hydrochloride salt.

If it is desired to prepare invention compounds in which $R^1$ is a $C_1$–$C_4$ alkyl radical, the amine prepared in Step C can be alkylated (Step D) to introduce the alkyl radical. In Step D, the amines of Formula I, where $R^1$ is a hydrogen atom, can be alkylated to give compounds of Formula I, in which $R^1$ is a lower alkyl radical, by treatment with an activated hydrocarbon, for instance methyl iodide, and a suitable base such as potassium carbonate. Typically 1 to 2 equivalents of alkylating agent is used, with 1 to 4 equivalents of base in a solvent such as dimethyl formamide. The reaction period is usually 1 to 24 hours at a temperature in the range of 60° C. to 150° C. Alternatively, the amine of Formula I, wherein $R^1$ is hydrogen, can be treated with formaldehyde in the presence of sodium cyanoborohydride in a solvent such as acidified acetonitrile, to introduce the methyl group. The product can then be recovered from the reaction by chromatographic techniques known in the art, such as flash chromatography. If desired, the amine can be converted to an acid addition salt, such as a hydrobromide or hydrochloride salt.

The cyclic ketone of Formula III which is used as starting material in Scheme I can be prepared by many synthetic pathways using procedures well known in the art of synthetic chemistry (see, for example, Chorvat et al., *J. Org. Chem.* 43:966 (1978)). One such procedure is depicted in Scheme II.

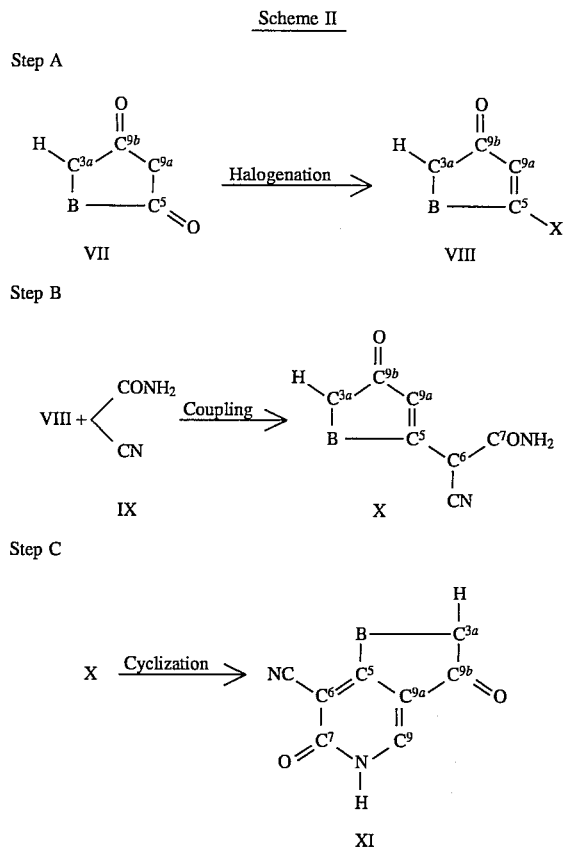

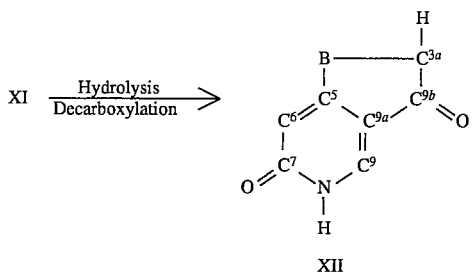

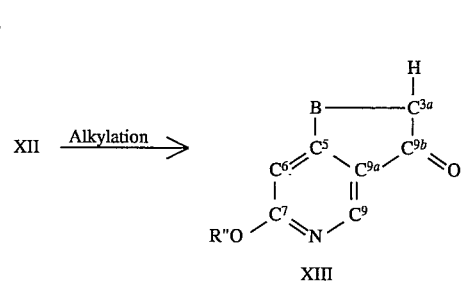

In Step A of Reaction Scheme II, a cyclic 1,3-diketone of Formula VII is subjected to a halogenation reaction thereby producing the chloro-enone of Formula VIII. In Step B of Reaction Scheme II, the chloro-enone is coupled to a nitrile amide of Formula IX producing the keto-nitrile-amide as described by Formula X. In Step C, the keto-nitrile-amide is cyclized to a nitrile pyridone of Formula XI by treatment with an acetal. In Step D, the nitrile pyridone is subjected to hydrolytic elimination of the nitrile group to yield pyridone of Formula XII. In Step E the pyridone is converted to an alkoxy pyridine of Formula XIII by an alkylation reaction.

There are many procedures which will affect the synthetic steps described in Scheme II. Suitable starting materials for use in Step A are cyclic 1,3-diketones in which B is represented by the same methylene or ethylene radical as that found in the desired cyclic ketone of Formula III. Examples of suitable synthetic transformations which lead to the desired products are described below in greater detail.

The halogenation reaction of Step A can be carried out using techniques well known in the art. Typically the cyclic 1,3-diketone of Formula VII is contacted with 0.3 to 0.5 equivalents of phosphorus trichloride in a suitable solvent (such as, for example, chloroform) at a temperature in the range of about 25° C. (~room temperature) up to solvent reflux for a period of 1 to 8 hours. The chloro-enone of Formula VIII can be recovered from the reaction using techniques known in the art such as extraction with an organic solvent, by chromatographic techniques, distillation, and the like.

The coupling reaction of Step B, in which the nitrile amide is reacted with the chloro-enone of Formula VIII, can be carried out using a variety of methods well known in the art. The chloro-alkene-one is typically contacted with 2 to 3 equivalents of cyanoacetamide of Formula IX in the presence of 2 to 3 equivalents of a suitable base (such as sodium hydride). The reactants are typically contacted in a solvent such as tetrahydrofuran at a temperature in the range of room temperature up to solvent reflux for a period of 1 to 8 hours. The resulting keto-nitrile-amide derivative of Formula X can be recovered from the reaction zone by suitable means, e.g., extraction as is known in the art. If desired, the keto-nitrile-amide can be further purified by recrystallization.

In Step C, keto-nitrile-amide of Formula X is subjected to a cyclization reaction. Typically one to two equivalents of a formaldehyde equivalent, such as dimethylformamide diethyl acetal, are contacted with the keto-nitrile-amide. The reaction can be carried out in an aprotic solvent such as dimethylformamide at room temperature for a period of 8 to 24 hours. The resulting nitrile pyridone of Formula XI can be purified by selective acid, base, and organic solvent extractions. If desired, the nitrile pyridone can be further purified by techniques known in the art such as recrystallization.

In Step D, the nitrile group of the nitrile pyridone of Formula XI is removed by hydrolysis to yield a pyridone of Formula XII. The nitrile-pyridone of Formula XI is typically contacted with an aqueous acid such as 48% hydrobromic acid at a temperature in the range of 60° C. up to solvent reflux for a period of time of 8 to 24 hours. The pyridone of Formula XII can be recovered from the reaction by selective acid, base, and organic solvent extractions. If desired, the pyridone can be further purified by techniques such as recrystallization.

The next step in the reaction sequence is to prepare the alkoxy pyridine derivative of the cyclic ketone of Formula XIII as depicted in Step E. The pyridone of Formula XII is alkylated by techniques known in the art. Typically the pyridone of Formula XII is treated with 0.4 up to 1 equivalent of silver carbonate, followed by contact with an alkylating agent such as methyl iodide. The reaction is allowed to proceed with 1 to 3 equivalents of alkylating agent in a solvent such as benzene at a temperature of reflux. The alkoxy pyridine of Formula XIII can be purified by chromatographic techniques known in the art such as flash chromatography or by recrystallization.

Another procedure which can be used to prepare the cyclic ketone of Formula III is described in Reaction Scheme III.

Scheme III

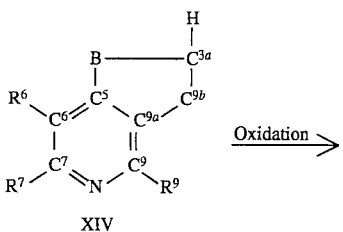

XIV

Oxidation

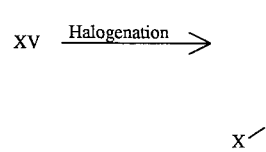

III

In Reaction Scheme III, a pyridine according to Formula XIV is oxidized, producing the cyclic ketone of Formula III. In the starting material (pyridine of Formula XIV), B is represented by the same methylene or ethylene function as that of the desired final product (Formula III). The oxidation reaction can be carried out using techniques well known in the art. Typically the pyridine of Formula XIV is contacted with potassium permanganate in suitable solvent such as acetic acid at a temperature in the range of about 0° C. to 60° C. for a period of about 0.5 up to 24 hours. The desired cyclic ketone of Formula III can be purified by chromatographic techniques known in the art (such as flash chromatography), recrystallization, and the like.

In some instances it is desirable to elaborate certain compounds described by Formula I into other compounds which are still encompassed by Formula I. There are many techniques well known in the art which can be used to achieve these transformations. For example, halogen may be introduced into the pyridine ring by the chemical steps described in Scheme IV.

Scheme IV

Step A

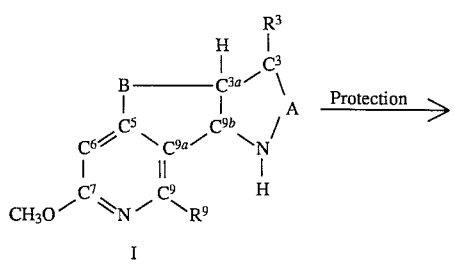

Step B

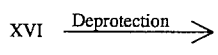

Step C

In Step A of reaction Scheme IV, the amine group of Formula I is subjected to a protection reaction in which a carbonate protecting group (Pg) is placed on the free amine, thereby producing the protected amine of Formula XV. In Step B, the protected amine is halogenated to halopyridine of Formula XVI. In Step C the halopyridine of Formula XVI is deprotected by removal of the carbonate protecting group to yield halopyridylamine of Formula I where X ($R^7$ in Formula I) is a halogen atom.

The protection reaction of Step A of Scheme IV can be carried out using techniques well known in the art. Typically the amine of Formula I is contacted with 1 to 1.5 equivalents of benzyl chloroformate at approximately room temperature in about 0.05 to 0.2 molar solution of sodium hydroxide. The reactants are typically stirred together for a period of time ranging from about 1 to 8 hours. The protected amine of Formula XV can then be recovered from the reaction using techniques known in the art such as extraction with an organic solvent and concentration.

The halogenation reaction of Step B, in which the alkoxy group of the protected pyridyl amine of Formula XV is converted to a halogen, can be carried out using methods known in the art. The protected pyridyl amine is typically contacted with 2 to 3 equivalents of phosphorous trichloride. The reactants are typically stirred together in an organic solvent such as dimethylformamide or pyridine at a temperature in the range of about 0° C. up to 120° C. for a period of time ranging from about 1 to 8 hours. The resulting halopyridine of Formula XVI can be purified by chromatographic techniques known in the art such as flash chromatography.

The deprotection reaction depicted in Step C can be carried out using techniques known in the art. This deprotection reaction serves to remove the benzyl carbonate protecting group (Pg). Typically, the halopyridine of Formula XVI is contacted with a stoichiometric amount of trimethysilyl iodide in a solvent such as methylene dichloride. The deprotection reaction is typically carried out at room temperature of 1 to 8 hours. The resulting halopyridyl amine of Formula I can be isolated and purified by well known procedures, such as chromatography or recrystallization.

In another example, compounds of Formula I in which $R_7$ is a $C_{1-4}$ alkyl radical, phenyl or substituted phenyl group can be prepared using methodology depicted in Scheme V.

Scheme V

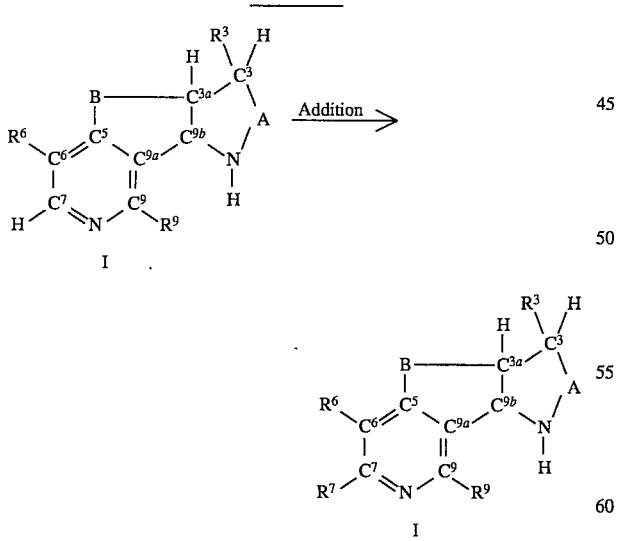

In Scheme V, an amine of Formula I (wherein $R^1$ and $R^7$ are both H) undergoes an addition reaction to give an amine of Formula I, wherein $R_7$ is a $C_{1-4}$ alkyl radical or phenyl or substituted phenyl group. Thus, the original amine (i.e., wherein $R^1$ and $R^7$ are both H) is contacted with an organometallic species to yield an amine of Formula I, wherein $R_7$ is a $C_{1-4}$ alkyl radical or phenyl or substituted phenyl group. The organometallic species employed is typically an alkyl derivative of an alkali metal, such as alkyllithium. The alkyl group employed typically corresponds to the desired group $R^7$ on Formula I. Typically two equivalents of organometallic (e.g., methyllithium) is contacted with the amine at a temperature in the range of −78° C. up to about room temperature. The reaction is allowed to proceed for 1 to 8 hours in an organic solvent such as tetrahydrofuran. The product can be purified by techniques known in the art such as flash chromatography.

Those of skill in the art recognize that the above-described synthetic schemes can be employed with a variety of starting materials, to produce many of the invention compounds. For example, compounds of formula XX

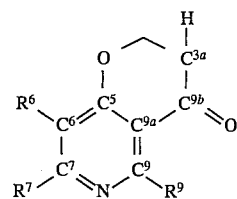

can be employed as starting materials in the procedure of Scheme I for the production of invention compounds.

Another procedure which can be used to prepare compounds embraced by Formula I is set forth in Scheme VI below. This scheme is useful for the preparation of compounds in which $R^6$ is not hydrogen.

Scheme VI

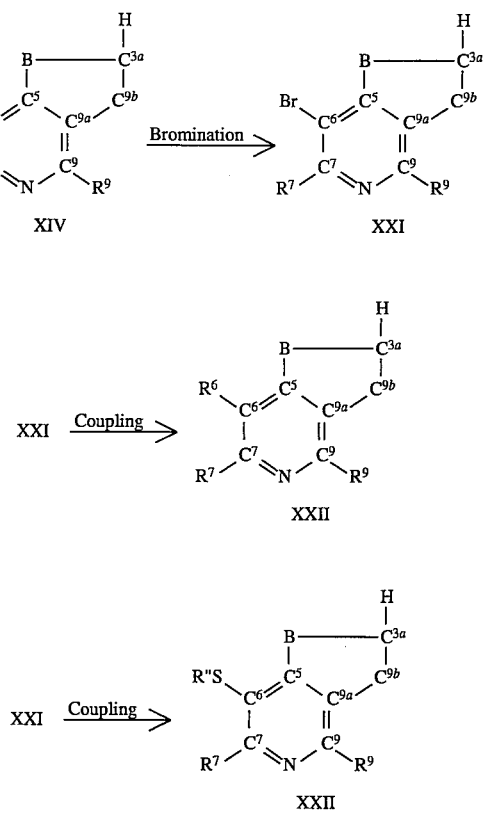

Step B

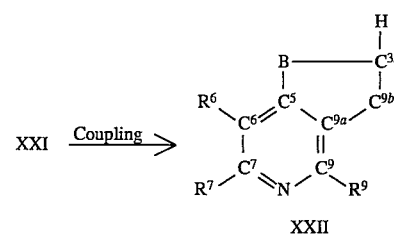

Step B'

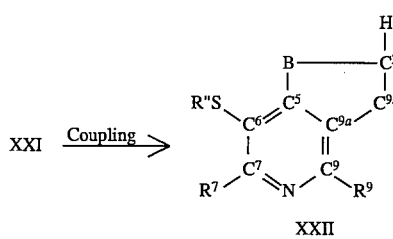

Compounds of Formula XXII can then be converted to compounds of Formula I employing reaction Scheme III, as described above, followed by reaction Scheme I, as described above.

In step A of Scheme VI, bromination of pyridine XIV leads to bromopyridine of Formula XXI. There are many well known procedures to introduce a bromine atom at the meta position of a pyridine ring. See, for example, Garcia et al., *J. Am. Chem. Soc.* 82:4430 (1960).

In step B, the bromine atom in Formula XXI can be displaced by $R^6$, wherein $R^6$ is selected from alkyl substituted alkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, and the like. Product is formed by a palladium-catalyzed crosscoupling reaction between the bromopyridine of Formula XXI and $R^6Br$ (wherein $R^6Br$ is based on $R^6$ as defined above, e.g., bromobenzene, 1-bromo-4-methoxybenzene, bromopropane, and the like).

In step B', the bromine atom in compounds of Formula XXI can alternatively be replaced with a group such as —SR" (see, for example, Brandsma et al. (1987) *Preparative Polar Organometallic Chemistry*, Vol. 1, Springer-Verlag, Berlin, p. 172). R" can be selected from hydrogen, lower alkyl, aryl, substituted aryl, alkylaryl, substituted alkylaryl, and the like.

In accordance with another embodiment of the present invention, there are provided pharmaceutical compositions comprising polycyclic fused ring compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers therefor) can be used in the manufacture of a medicament for modulating the activity of acetylcholine receptors.

Pharmaceutically acceptable carriers contemplated for use in the practice of the present invention include carriers suitable for oral, intravenous, subcutaneous, transcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, patches, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Invention compounds can optionally be converted into non-toxic acid addition salts. Such salts are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Such salts can readily be prepared employing methods well known in the art.

In accordance with yet another embodiment of the present invention, there are provided methods of modulating the activity of acetylcholine receptors within a cell, said method comprising:

contacting a cell containing acetylcholine receptors with a concentration of a polycyclic fused ring compound as described above sufficient to modulate the activity of acetylcholine receptors within said cell.

As employed herein, the phrase "modulating the activity of acetylcholine receptors" refers to a variety of therapeutic applications, such as the treatment of Alzheimer's disease and other disorders involving memory loss and/or dementia (including AIDS dementia); disorders of extrapyramidal motor function such as Parkinson's disease, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulimia and anorexia; disorders of nociception and control of pain; autonomic disorders including dysfunction of gastrointestinal motility and function such as irritable bowel syndrome, diarrhea, constipation, gastric acid secretion and ulcers; pheochromocytoma; cardiovascular dysfunction including hypertension and cardia arrhythmias, comedication in surgical procedures, and the like.

The compounds of the present invention are especially useful for the treatment of Alzheimer's disease as well as other types of dementia (including dementia associated with AIDS), Parkinson's disease, attention deficit syndrome, and for the control of pain. Thus modulation of the activity of acetylcholine receptors within the cells of a patient suffering from any of the above-described indications will impart a therapeutic effect.

As employed herein, the phrase "an effective amount", when used in reference to compounds of the invention, refers to levels of compound sufficient to provide circulating concentrations high enough to impart a beneficial effect on the recipient thereof. Such levels typically fall in the range of about 0.01 up to 100 mg/kg/day; with levels in the range of about 1 up to 50 mg/kg/day being preferred.

The invention will now be described in greater detail by reference to the following non-limiting examples.

EXAMPLE 1

Preparation of Nitroketone V (Z=NO$_2$)

Into a 250 mL three-necked round-bottomed flask fitted with a mechanical stirrer, dropping funnel, a thermometer and flushed with nitrogen was placed 3-methoxy-8-oxo-5,6,7,8-tetrahydroisoquinoline III (Chorvat et al., *J. Org. Chem.* 43:966 (1978)) (5 g; 28 mmole) and dry tetrahydrofuran (THF; 40 mL). The solution was cooled to −78° C. and lithium diisopropylamide (LDA; 34 mmole; 17 mL, 2M) was added dropwise. The resulting yellow brown solution was stirred at −78° C. for 30 minutes and a solution of ZnCl$_2$ in Et$_2$O (34 mmole 34 mL, 1M) was added. The resulting mixture was stirred for 1 hour at −78° C. and nitroethylene (Ranganathan et al., *J. Org. Chem.* 45:1185 (1980)) (34 mmole; 2.48 g) previously dissolved in dry THF (5 mL) was added such that the temperature did not rise above −60° C. After 3 hours at this temperature the solution was hydrolyzed with aqueous acetic acid (10%) (50 mL). The mixture was extracted with CH$_2$Cl$_2$ (3×50 mL), dried (MgSO$_4$) and concentrated under reduced pressure. The crude material was purified via chromatography on silica using $CHCl_3$ as eluant giving 6.8 g of the final product as a brown oil contaminated with 7% of starting material (89%) $^1H$ NMR (300 MHz, $CDCl_3$): δ8.80 (s, 1H), 6.56 (s, 1H), 4.67 (t, J=7 Hz, 2H), 3.98 (s, 3H), 2.95 (m, 2H), 2.55 (m, 2H), 2.12 (m, 2H), 1.90 (m, 1H).

EXAMPLE 2

Preparation of the Tricyclic Imine VI

Raney Ni (6 g of the wet catalyst washed with methanol prior to use) was added to nitroketone V (6.8 g) dissolved in methanol (MeOH; 20 mL) and the resulting mixture was hydrogenated under 50 psi of $H_2$ in Parr apparatus for 12 hours. The crude mixture was then filtered through celite, concentrated under reduced pressure and purified via chromatography on silica using $CHCl_3$/MeOH (99/1) as eluant, giving 4.18 g (20.6 mmole, 82%) of the pure imine as an oil. 1H NMR (300 MHz, $CDCl_3$) δ8.88 (s, 1H), 7.27 (s, 1H), 4.19–4.11 (m, 1H) 3.95 (s, 3H), 3.77–3.65 (m, 1H), 2.99–2.81 (m, 3H), 2.33–2.23 (m, 2H), 1.65–1.48 (m, 2H).

EXAMPLE 3

Preparation of the Tricyclic Amine I

Imine VI (4.18 g, 20.6 mmole), sodium cyanoborohydride (2.59 g, 41.3 mmole), methanol (20 mL) and a trace of bromocresol green indicator were introduced into a 100 mL one-necked round-bottomed flask. To this blue solution was added dropwise 2N HCl in dioxane such that the yellow end point was barely maintained. The resultant yellow solution was stirred 20 minutes at room temperature followed by addition of 2N HCl in dioxane (5 mL). The solution was stirred for one more hour at room temperature and concentrated under reduced pressure. To the resulting crude material was added water (20 mL), the solution was basified with aqueous NaOH (1N) and extracted with $CH_2Cl_2$ (3×50 mL). The organic layers were combined, dried ($MgSO_4$) and concentrated under reduced pressure. The crude material was purified via chromatography on silica using $CHCl_3$ to $CHCl_3$/MeOH 95/5 as eluant, yielding 2.51 g (12 mmole, 59%) of the pure compound as a colorless oil. $^1H$ NMR (300 MHz, $CDCl_3$) δ8.46 (s, 1H), 7.42 (s, 1H), 4.80 (d, J=7 Hz, 1H), 4.11 (s, 3H), 3.37 (m, 2H), 3.21–3.05 (m, 2H), 2.95–2.68 (m, 2H), 2.33 (m, 1H), 1.86 (m, 2H), 1.60 (m, 1H). A sample was converted to as the dihydrobromide salt; mp>250° C. Anal. ($C_{12}H_{16}N_2O.2HBr$) C, H, N.

EXAMPLE 4

Akylation of the Tricyclic Methylamine I

To a stirred, cooled solution of the tricyclic amine I (314 mg, 1.54 mmole) in $CH_3CN$ (15 mL) was added aqueous formaldehyde (37% 16 mL) and sodium cyanoborohydride (200 mg; 3.18 mmole). After stirring at 0° C. for 30 minutes, acetic acid (0.3 mL) was introduced and the crude mixture was stirred at room temperature overnight. The resulting solution was concentrated under reduced pressure, the residue was taken into $H_2O$ (25 mL) and then basified with NaOH (1N). The aqueous solution was extracted with $CH_2Cl_2$ (3×20 mL). The combined organic layers were dried ($MgSO_4$) and concentrated under reduced pressure yielding a yellow oil. The crude mixture was purified via chromatography on silica using $CHCl_3$/MeOH 9/1 as eluant yielding 202 mg (0.92 mmole, 60%) of the desired product. $^1H$ NMR (300 MHz, $CDCl_3$) δ7.87 (s, 1H), 6.55 (s, 1H), 3.91 (s, 3H), 3.06 (t, J=7 Hz, 1H), 2.99 (d, J=8.5 Hz, 1H), 2.79 (m, 2H), 2.52 (m, 1H) 2.27 (s, 3H), 2.20 (m, 1H) 2.08 (m, 1H), 1.68 (m, 2H), 1.55 (m, 1H).

EXAMPLE 5

Preparation of the Heterocyclic Amine

Following chemistry described in Scheme I, and using the heterocyclic ketone XX (instead of cyclic ketone III as illustrated in the Scheme; see Cordonnier & Sliva, *J. Chem. Res.*(S), 124 (1979)) was converted to the heterocyclic amine I which was obtained as a white solid $^1H$ NMR (300 MHz, $CDCl_3$) δ8.53 (s, 1H), 8.29 (d, J=6 Hz, 1H), 6.79 (d, J=6 Hz, 1H), 4.18 (dd, J=Hz and 11 Hz, 2H), 3.98 (d, J=6 Hz, 1H), 3.63 (t, J=11 Hz, 1H), 3.12 (m, 1H), 2.99 (m, 1H), 2.50 (m, 1H), 2.15 (m, 1H), 1.91 (brs, 1H), 1.50 (m, 1H).

EXAMPLE 6

Preparation of the Cyanoketone V (Z=CN)

3-Methoxy-8-oxo-5,6,7,8-tetrahydoisoquinoline (531 mg, 3 mmol) and pyrrolidine (1.5 mL, 18 mmol) were dissolved in anhydrous diethyl ether (25 mL) with stirring under inert atmosphere at −10° C. Titanium tetrachloride (3 mL of a 1M solution in $CH_2Cl_2$, 3 mmol) was added, keeping the internal temperature below 0° C. After the addition, the mixture was allowed to warm to 25° C. and after 30 minutes the reaction mixture was filtered under inert atmosphere. The precipitate was washed with dry diethyl ether (10 mL) and the filtrate concentrated in vacuo. After pumping under high vacuum for 1 h, anhydrous dioxane (15 mL) and acrylonitrile (10 mL) were introduced and the solution heated at reflux for 3 h under inert atmosphere. A further aliquot of acrylonitrile (5 mL) was added and the mixture stirred at 25° C. for 18 h. Water (10 mL) was added and the mixture heated under reflux for 45 minutes. The cooled mixture was concentrated in vacuo, water (50 mL) added and the resulting mixture extracted with $CH_2Cl_2$ (3×30 mL). The combined organic extracts were washed with brine (20 mL), dried ($Na_2SO_4$) and concentrated in vacuo. The residue was chromatographed on silica gel with ethyl acetate:hexane (1:9, 1:4) as eluant to afford recovered 3-methoxy-8-oxo-5,6,7,8-tetrahydoisoquinoline (225 mg) and the product (159 mg, 40%) based on recovered starting material. $^1H$ NMR ($CDCl_3$, 300 MHz): δ8.81 (s, 1 H), 6.56 (s, 1H), 3.99 (s, 3H), 2.99 (m, 2H), 2.64 (m, 3H), 2.26 (m, 2H), 1.87 (m, 2H).

EXAMPLE 7

Preparation of the Tricyclic Amine I (A=$CH_2CH_2$)

Raney nickel (approximately 100 mg of a neutral aqueous slurry, Aldrich) was washed twice with water, twice with 2-propanol and twice with methanol. A Parr hydrogenation bottle was charged with the washed Raney nickel catalyst and the nitrile V (121 mg, 0.53 mmol) dissolved in methanol (40 mL). The agitated mixture was hydrogenated at 54 psi and 25° C. for 18 h. Analysis by GCMS at this point indicated approximately equal amounts of cyclized imine and cis and trans ring junction isomeric amines. Hydrogenation was therefore continued at 40 psi for two days. The catalyst was removed by filtration through Celite™ and the filtrate concentrated in vacuo. The residue was chromatographed on silica gel with ethyl acetate, then methanol:ethyl acetate (1:9, 1:4) as eluants to afford the product (73 mg, 63%) as an approximately (1:1) mixture of cis and trans ring junction isomers. $^1$H NMR (CDCl$_3$, 300 MHz): δ8.28 (s, 1H), 8.03 (s, 1H), 6.46 (s, 1H), 6.43 (s, 1H), 3.89 (s, 3H), 3.88 (s, 3H), 3.76 (d, J=3.5 Hz, 1H), 3.35 (d, J=9 Hz, 1H), 3.25 (dt, J=13, 2.5 Hz, 1H), 3.0 (dt, J=13, 2.5 Hz, 1H), 2.90 (m, 6H), 2.20 (m, 1H), 1.2–1.9 (m, 13H).

EXAMPLE 8

Radioligand Binding $^3$H-Nicotine binding to rat cerebral membranes was performed according to modifications of the method of Flyn and Mash (*J. Neurochem.* 37:1948 (1986)). $^3$H-Nicotine (80 ci/mmol; New England Nuclear Corporation, Boston, Mass.) was used as the ligand for acetylcholine receptor binding assays. All other reagents were purchased from the Sigma Chemical Co. (St. Louis, Mo.).

Male Sprague-Dawley rats (250–400 gm) were sacrificed by decapitation, the brains removed and the cerebral cortex dissected on ice. Synaptic membranes were prepared by homogenizing the cortical tissue in 20 volumes of ice-cold modified Tris buffer (50 mM Tris pH 7.4, 120 mM NaCl, 5 mM KCl, 2 mM EDTA, 1 mM PMSF) with a polytron (20 sec at setting 5–6) followed by centrifugation (15 min at 25,000×g) at 4° C. The resultant pellet was rehomogenized and centrifuged twice. The final pellet was resuspended in ice-cold assay buffer (50 mM Tris pH 7.4, 120 mM NaCl, 5 mM KCl, 2 mM CaCl$_2$, 1 mM MgCl$_2$) at a concentration of membrane equivalent to 1 gm wet weight cortex per 10 ml buffer. After protein determination the final membrane preparation was diluted with buffer to 3 mg protein/ml. This membrane preparation was used in either the fresh state or frozen then thawed.

The binding assay is performed using 96-well plates and a Biomek automated work station (Beckman Instrument Co.). $^3$H-Nicotine was diluted in assay buffer to give a final concentration of 1.9 nM. The Biomek automated work station was programmed to automatically transfer 750 μl of assay buffer with $^3$H-nicotine, 230 μl of membrane preparation and 20 μl of solution containing the compound of interest in assay buffer or ethanol:DMSO 1:1) or appropriate vehicle to the 96-well plate. Atropine was added to the incubation buffer at a final concentration of 3 μM to block binding to muscarinic acetylcholine receptor sites. The plates were maintained on ice for 60 min and the tissue-bound radioactivity was separated from the free by rapid filtration in a Brandel Harvester onto GF/C filters presoaked in 0.5% polyethyleneimine for at least 2 hr. The filters were washed with 4×2 ml of ice-cold assay buffer and filters were transferred to vials to which 4 ml of scintillation cocktail was added. The radioactivity was measured in a LS-6500 Beckman Liquid Scintillation Counter in an autodpm mode. Data were analyzed by log-logit transformation to give IC$_{50}$ values. Non-specific binding was defined by 10 μM cytisine.

The ability of invention compounds to displace $^3$H-QNB (quinuclidinyl benzilate; 43 Ci/mmol), $^3$H-cyt (cytisine; 31 Ci/mmol) or $^3$H-MCC (methylcarbamylcholine; 78 Ci/mmol) from rat cerebral membranes can also be tested using the above-described method in which $^3$H-nicotine is replaced with any one of these radiolabeled acetylcholine receptor ligands.

The results of $^3$H-nicotine, $^3$H-QNB, $^3$H-cyt and $^3$H-MCC binding displacement assays of several invention compounds are summarized in Table I.

TABLE I

| Compound tested, Formula I, wherein— | IC$_{50}$, μM | | | |
|---|---|---|---|---|
| | QNB[a] | CYT[b] | NIC[c] | MCC[d] |
| R$^1$, R$^3$, R$^6$, R$^9$ = H; R$^7$ = OCH$_3$; A = —CH$_2$—, B = —CH$_2$CH$_2$— | 6 | 5.4 | 1.9 | 0.8 |
| R$^1$, R$^3$, R$^6$, R$^7$, R$^9$ = H; A = —CH$_2$—, B = —OCH$_2$— | NA | 2 | 0.51 | 0.61 |
| R$^1$ = —CH$_3$; R$^7$ = OCH$_3$; R$^3$, R$^6$, R$^9$ = H; A = —CH$_2$—, B = —CH$_2$CH$_2$— | 9 | 27.5 | 10.7 | 5.5 |

[a] QNB is quinuclidinyl benzilate
[b] CYT is cystine
[c] NIC is nicotine
[d] MCC is methylcarbamylcholine
[e] NA means the compound was tested but displayed no activity in the test system.

As evidenced by the micromolar IC$_{50}$ values in the Table, each of the compounds tested was able to displace acetylcholine receptor ligands from their binding sites in rat cerebral membranes.

EXAMPLE 9

Neurotransmitter Release

Measurement of $^3$H-dopamine release from rat striatal slices was performed according to the method of Sacaan et al. (*J. Neurochem.* 59:245 (1992)). Male Sprague-Dawley rats (250–300 g) were decapitated and the striata dissected quickly on a cold glass surface. The tissue was chopped to a thickness of 300 μm with a McIlwain tissue chopper. After chopping again at right angles the tissue was dispersed and incubated for 10 min. at 37° C. in oxygenated Kreb's buffer. $^3$H-Dopamine (40 Ci/mmol, NEN-Dupont, Boston, Mass.) was added (50 nM) and the tissue was incubated for 30 min. in Kreb's buffer containing 10 μM pargyline and 0.5 mM ascorbic acid. Aliquots of the minced tissue were then transferred to chambers of a Brandel Superfusion system in which the tissue was supported on Whatman GF/B filter discs. The tissue was then superfused with buffer at a constant flow rate of 0.3 ml/min. by means of a Brandel peristaltic pump. The perfusate was collected in plastic scintillation vials in 3-min. fractions, and the radioactivity was estimated by scintillation spectrophotometry. The superfusate for the first 120 min. was discarded. After two baseline fractions had been collected, the superfusion buffer was switched to fresh buffer with or without compound of interest. At the end of the experiment the filter and the tissue were removed, and the $^3$H-dopamine content was estimated after extraction into scintillation fluid. The fractional efflux of tritium was estimated as the amount of radioactivity in the perfusate fraction relative to the total amount in the tissue.

Following essentially the same procedure as set forth in the preceding paragraph, the amount of $^3$H-norepinephrine released from rat hippocampus and thalamus slices superfused with buffer containing (or lacking) compounds of interest was also measured.

The results of studies of the effects of an invention compound (as compared to the effect of nicotine and cytisine) on the release of neurotransmitters from rat brain slices are presented in Table II. The results presented in the Table are expressed as the percent fractional release.

TABLE II

Ligand-stimulated $^3$H-neurotransmitter Release
in vitro from Slices of Different Rat Brain Regions

| LIGAND | $^3$H-DOPAMINE STRIATUM | $^3$H-NOREPINE-PHRINE HIPPOCAMPUS | $^3$H-NOR-EPINEPHINE THALAMUS |
|---|---|---|---|
| NICOTINE (100 μM) | 1.80 | 4.1 | 2.9 |
| CYTISINE (100 μM) | 0.96 | 4.3 | 2.9 |
| Compound[a] (300 μM) | 2.2 | 0.69 | 2.2 |

[a]Compound tested is Formula I, wherein $R^1$, $R^3$, $R^6$, $R^9$ = H; $R^7$ = —OCH$_3$—; A = —CH$_2$—, B = —CH$_2$CH$_2$—

As shown in Table II, the invention compound selectively induces release of catecholamines in different brain regions.

EXAMPLE 10

6-Hydroxydopamine Lesion Model of Parkinsonism

The effects of invention compounds on turning behavior of rats with unilateral 6-hydroxydopamine lesions in the striatum were evaluated using the procedure of Ungerstedt and Arbutknott *Brain Res.* 24:485–493 (1970). Rats were injected with desmethylimipramine (25 mg/kg i.p.) and pargyline (75 mg/kg i.p.) approximately 30 minutes prior to 6-hydroxydopamine infusion into the substantia nigra. The results of one such study are shown in Table III. Results reported in the Table are measured as the maximal rotation per 15-min interval toward the lesioned side of the striatum.

TABLE III

Induction of turning in rats with unilateral
6-hydroxydopamine lesions of the nigro-striatal
dopamine pathway

| COMPOUND | RANGE OF ACTIVITY |
|---|---|
| NICOTINE (1 mg/kg, s.c.) | 6–50 |
| AMPHETAMINE (5 mg/kg, s.c.) | 50–200 |
| COMPOUND[a] (10 mg/kg, s.c.) | 9–50 |

[a]Compound tested is Formula I, wherein
$R^1$, $R^3$, $R^6$, $R^9$ = H;
$R^7$ = —OCH$_3$—;
A = —CH$_2$—;
B = —CH$_2$CH$_2$—

As shown in Table III, the invention compound induces turning towards the 6-hydroxydopamine-lesioned side of the rat striatum in a manner consistent with the in vivo release of dopamine from striatal dopamine nerve terminals.

EXAMPLE 11

Haloperidol-Induced Catalepsy Model

The effects of invention compounds on haloperidol-induced catalepsy in rats were evaluated using the procedure of Emerich et al., *Pharmacol. Biochem. Behav.* 38:875–880 (1991). Nicotine (as the tartrate salt) and invention compound (as the free salt) were given i.p. 10 minutes before injection of haloperidol (2 mg/kg i.p.). Catalepsy measurements were taken 15, 30, 60, 90, 120 and minutes post-haloperidol injection. The percent reduction in catalepsy was calculated based on rats treated with halperidol alone. The results of one such study are shown in Table IV. Results are expressed in the Table as the maximum reduction in catalepsy.

TABLE IV

Prevention of haloperidol-induced catalepsy in rats

| COMPOUND | REDUCTION IN CATALEPSY (%) |
|---|---|
| NICOTINE (2 mg/kg, s.c.) | 21 |
| COMPOUND[a] (3 mg/kg, s.c.) | 34 |

[a]Compound tested is Formula I, wherein
$R^1$, $R^3$, $R^6$, $R^9$ = H;
$R^7$ = —OCH$_3$—;
A = —CH$_2$—;
B = —CH$_2$CH$_2$—

As shown in Table IV, the invention compound reduces the cataleptogenic effect of haloperidol in rats.

EXAMPLE 12

Tail Flick Assay for Analgesic Potential

The effects of invention compounds on latency in the time between stimulus application and tail flick in rats were evaluated using the procedure of D'Amour and Smith, *J. Pharmacol. Exp. Ther.* 72:74–79 (1941). Male rats (150–200g; Harlan, San Diego, Calif.) were acclimated to investigator's handling by taking two-to-three tail-flick latencies. The animals were held by hand such that the tail is placed in the groove of the Tail-Flick meter (IITC Life Sciences, Woodland Hill, Calif., Model 33). The light was focused 3–4 cm from the tip of the tail by a foot-operated switch. The intensity of the incident beam was adjusted to give baseline latencies in the range of 1–4 seconds. Groups of 5–6 rates were used in each treatment. The tail-flick latencies were recorded to the nearest 0.1 seconds and a cut-off time of 10 seconds was established to prevent thermal injury. The results of one such study are shown in Table V. Results presented in the Table are expressed as the percent of the maximum latency to remove the tail from the light beam. Maximum latency is 10 seconds.

TABLE V

Tail flick assay in the rat

| COMPOUND | % MAXIMUM POSSIBLE EFFECT | DURATION OF EFFECT |
|---|---|---|
| Nicotine (1 mg/kg, p.o.) | 38% | 60 min |
| Morphine (2 mg/kg, s.c.) | 100% | 60 min |
| Compound[a] (30 mg/kg, p.o.) | 52% | >180 min |

[a]Compound tested is Formula I, wherein
$R^1$, $R^3$, $R^6$, $R^9$ = H;
$R^7$ = —OCH$_3$—;
A = —CH$_2$—;
B = —CH$_2$CH$_2$—

As shown in Table V, the invention compound increased the latency period, as compared to nicotine, between application of stimulus and the tail-flick response with a longer duration than the effect of morphine.

While the invention has been described in detail with reference to certain preferred embodiments thereof, it will be understood that modifications and variations are within the spirit and scope of that which is described and claimed.

That which is claimed is:

1. A compound having the structure:

wherein:

A is a 1 or 2 atom bridging species which forms part of a 5- or 6-membered ring including $N^1$, $C^{9b}$, $C^{3a}$ and $C^3$; and B is a 1, 2 or 3 carbon alkylene or oxyalkylene bridging species which forms part of a 5-, 6- or 7-membered ring including $C^5$, $C^{9a}$, $C^{9b}$ and $C^{3a}$; and $R^1$ is selected from hydrogen, lower alkyl, aryl, substituted aryl, alkylaryl, or substituted alkylaryl, or $R^1$ is absent when there is a double bond between $N^1$ and $C^{9b}$; and $R^3$ is selected from hydrogen or a lower alkyl moiety; and $R^6$ and $R^7$ are independently selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heteroaryl, substituted heteroaryl, acyl, halogen, trifluoromethyl, trialkylsilyl, triarylsilyl, cyano, nitro, —S(O)—R', S(O)$_2$R', —S(O)$_2$—NHR', —C(O)—NHR', or —NH—C(O)—R', wherein each R' is lower alkyl or aryl; —OR", —NR"$_2$ or —SR", wherein each R" is independently selected from hydrogen, lower alkyl, aryl, substituted aryl, alkylaryl or substituted alkylaryl; and $R^9$ is selected from hydrogen or lower alkyl;

with the proviso that, when A is —CH$_2$—, B is —CH$_2$CH$_2$—, and each of $R^3$, $R^6$, $R^7$ and $R^9$ are —H, then $R^1$ is not —H, —CH$_3$ or —CH$_2$CH$_3$.

2. A compound according to claim 1 wherein A is a 1 or 2 atom bridging species selected from alkylene, —C(O)— or —C(O)-substituted alkylene.

3. A compound according to claim 1 wherein A is selected from —CH$_2$—, or —CH$_2$—CH$_2$—.

4. A compound according to claim 1 wherein B is —OCH$_2$— or —CH$_2$CH$_2$—.

5. A compound according to claim 1 wherein $R^1$ is selected from hydrogen, methyl or benzyl.

6. A compound according to claim 1 wherein $R^3$ is hydrogen.

7. A compound according to claim 1 wherein $R^6$ is selected from hydrogen, halogen, alkyl, alkenyl, alkynyl, aryl, or substituted aryl.

8. A compound according to claim 1 wherein $R^7$ is selected from hydrogen, alkyl or alkoxy.

9. A compound according to claim 1 wherein $R^9$ is hydrogen.

10. A compound according to claim 1 wherein said compound is substantially optically pure.

11. A compound according to claim 1 wherein said compound is a racemic mixture.

12. compound according to claim 1 wherein:

A=—CH$_2$—,
B=—CH$_2$CH$_2$—,
$R^1$=—H,
$R^3$=—H,
$R^6$=—H,
$R^7$=—OCH$_3$, and
$R^9$=—H.

13. A compound according to claim 1 wherein:

A=—CH$_2$—,
B=—O—CH$_2$—,
$R^1$=—H,
$R^3$=—H,
$R^6$=—H,
$R^7$=—H, and
$R^9$=—H.

14. A compound according to claim 1 wherein:

A=—CH$_2$—,
B=—CH$_2$CH$_2$—,
$R^1$=—CH$_3$,
$R^3$=—H,
$R^6$=—H,
$R^7$=—O—CH$_3$, and
$R^9$=—H.

15. A compound according to claim 1 wherein:

A=—CH$_2$CH$_2$—,
B=—CH$_2$CH$_2$—,
$R^1$=—H,
$R^3$=—H,
$R^6$=—H,
$R^7$=—OCH$_3$, and
$R^9$=—H.

16. A pharmaceutical composition comprising a compound having the structure:

wherein:

A is a 1 or 2 atom bridging species which forms part of a 5- or 6-membered ring including $N^1$, $C^{9b}$, $C^{3a}$ and $C^3$; and B is a 1, 2 or 3 carbon alkylene or oxyalkylene bridging species which forms part of a 5-, 6- or 7-membered ring including $C^5$, $C^{9a}$, $C^{9b}$ and $C^{3a}$; and $R^1$ is selected from hydrogen, lower alkyl, aryl, substituted aryl, alkylaryl, or substituted alkylaryl, or $R^1$ is absent when there is a double bond between $N^1$ and $C^{9b}$; and $R^3$ is selected from hydrogen or a lower alkyl moiety; and $R^6$ and $R^7$ are independently selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, aroyl, substituted aroyl, heteroaryl, substituted heteroaryl, acyl, halogen, trifluoromethyl, trialkylsilyl, triarylsilyl, cyano, nitro, —S(O)—R', —S(O)$_2$—R', —S(O)$_2$—NHR', —C(O)—NHR', or —NH—C(O)—R', wherein each R' is lower alkyl or aryl; —OR", —NR"$_2$ or —SR", wherein each R" is independently selected from hydrogen, lower alkyl, aryl, substituted aryl, alkylaryl or substituted alkylaryl; and $R^9$ is selected from hydrogen or lower alkyl;

with the proviso that, when A is —CH$_2$—, B is —CH$_2$CH$_2$—, and each of $R^3$, $R^6$, $R^7$ and $R^9$ are —H, then $R^1$ is not —H, —CH$_3$ or —CH$_2$CH$_3$, and a pharmaceutically acceptable carrier therefor, wherein said compound is optionally in the form of a pharmaceutically acceptable non-toxic acid addition salt.

17. A method of modulating the activity of acetylcholine receptors within a cell, said method comprising:

contacting a cell containing acetylcholine receptors with a sufficient concentration of a compound according to claim 1 to modulate the activity of acetylcholine receptors within said cell.

* * * * *